(12) United States Patent
Akatsuka et al.

(10) Patent No.: US 6,500,322 B2
(45) Date of Patent: Dec. 31, 2002

(54) GAS SENSOR

(75) Inventors: Shoji Akatsuka, Aichi (JP); Kouji Matsuo, Aichi (JP); Masahiro Asai, Aichi (JP); Satoshi Ishikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/729,112

(22) Filed: Dec. 5, 2000

(65) Prior Publication Data

US 2001/0002651 A1 Jun. 7, 2001

(30) Foreign Application Priority Data

Dec. 6, 1999 (JP) ............................................. 11-346362
Jan. 27, 2000 (JP) ........................................ 2000-018576

(51) Int. Cl.[7] ........................................... G01N 27/407
(52) U.S. Cl. ..................................... 204/427; 204/428
(58) Field of Search ................................. 204/421–429

(56) References Cited

U.S. PATENT DOCUMENTS 3,445,369 A * 5/1969 Porter et al.
4,116,797 A 9/1978 Akatsuka
4,786,399 A * 11/1988 Wertheimer et al.
5,900,129 A 5/1999 Tsuji et al.

FOREIGN PATENT DOCUMENTS

| JP | 60-42912 | 9/1985 |
| JP | 9-54063 | 2/1997 |

* cited by examiner

Primary Examiner—T. Tung
(74) Attorney, Agent, or Firm—Sughrue Mion, PLLC

(57) ABSTRACT

A gas sensor including a detecting element having electrodes on first and second surfaces of an oxygen ion conductive solid-state electrolyte; a main fitting having a fitting portion to be fitted into a mounting hole formed on a wall of the pipe defining a flow path for a gas-to-be-measured for holding the detecting element in such manner that the first surface is disposed via the mounting hole at an inner position of the pipe with respect to the fitting portion; a cylindrical cover of which one end is connected to an outer position of the pipe with respect to the fitting portion of the main fitting and the other end is provided with a cylindrical sealing member having an air hole for introducing air to the second surface on one end and a through hole through which a lead connected to both electrodes of the detecting element passes on the other end; and a water repellant filter having gas permeability for closing the air hole, characterized in that the water repellant filter is formed in a sheet shape and mounted on the air hole by means of an inserting member that can be inserted in the air hole.

25 Claims, 12 Drawing Sheets

Fig. 3
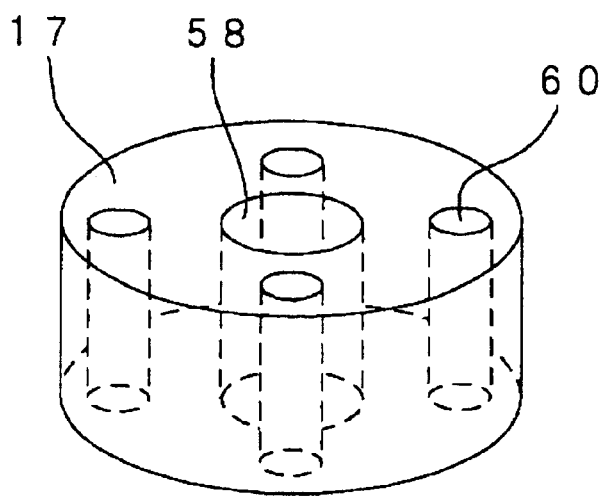
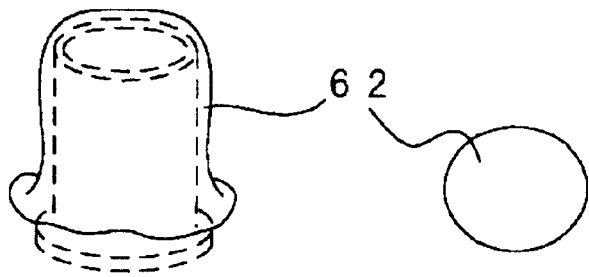
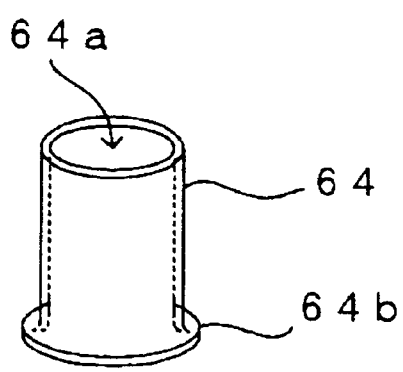

Fig. 10 (a)  320, 320a
Fig. 10 (b)  320, 320a, 320b
Fig. 10 (c)  320, 320c, 320d
Fig. 10 (d)  320, 320e
Fig. 10 (e)  320g, 320, 320f
Fig. 10 (f)  320, ROUGHENED SURFACE
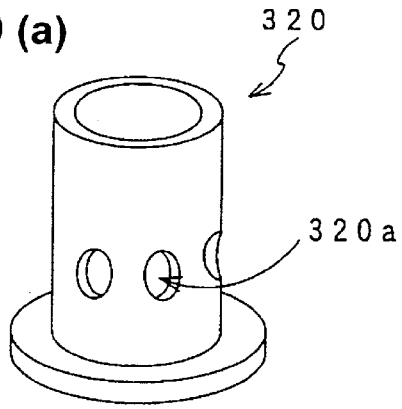
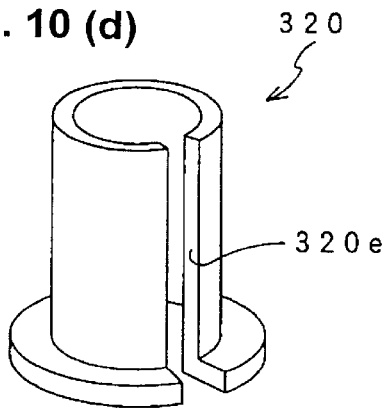
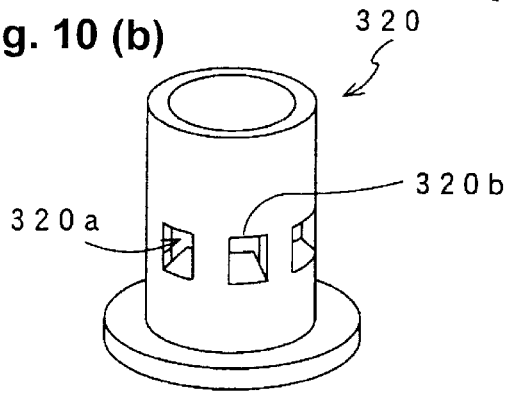
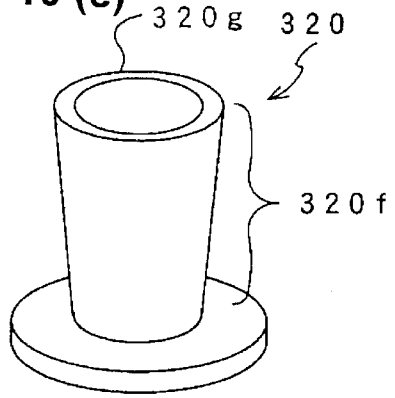
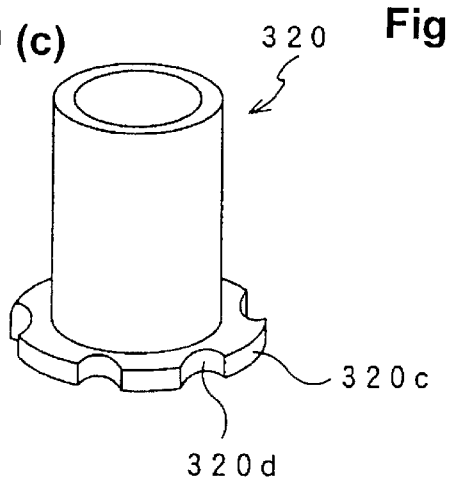
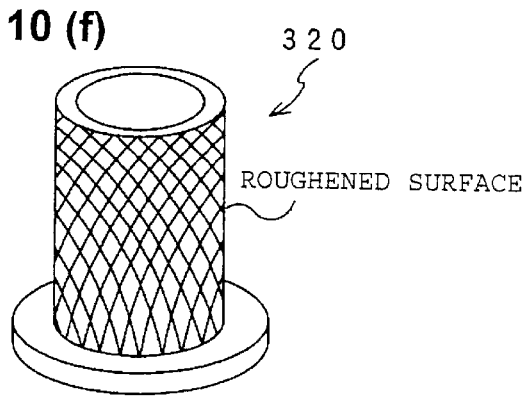

ENLARGEMENT OF PORTION A

GAS SENSOR

BACKGROUND OF THE INVENTION

1. Field of the Invention

The present invention relates to a gas sensor for mounting in a pipe defining a flow path in which a gas-to-be-measured such as an exhaust gas flows, and functions by introducing air as a reference gas from the outside.

2. Description of the Related Art

In the related art, various kinds of sensors such as an HC sensor or an NOx sensor are known as gas sensors for detecting the density of a specific gas component in a mixed gas. For example, as shown in FIG. 12, an oxygen sensor 501 comprising a detecting element 502 formed of an oxygen ion conductive solid-state electrolyte is known.

The detecting element 502 described above comprises an internal electrode 503 and an external electrode 504 formed respectively on the inner and outer surfaces of the element body of a cylindrical shape with a bottom wherein one end is closed by a solid-state electrolyte and the other end is left open. Between the internal electrode 503 and the external electrode 504, an electromotive force is generated depending on the difference in the concentration or partial pressure of oxygen between the internal space in the detecting element 502 formed in a cylindrical shape and the outside. For example, the concentration of oxygen in a gas-to-be-measured can be detected by inserting the closed end of the detecting element 502 into the interior of the pipe defining a flow path of a gas-to-be measured via a cylindrical main fitting 505 to allow the external electrode 504 to come into contact with a gas-to-be-measured and the internal electrode 503 with the air, and then detecting an electromotive force generated between the internal electrode 503 and the external electrode 504.

Introduction of air into the oxygen sensor may be carried out via a clearance formed in twisted core wires of a lead 507. However, in order to introduce a large amount of air, a method of forming an air hole 509 on the side surface of a cylindrical cover 506 and plugging it by a water repellant filter 508 having gas permeability formed, for example, of a fluorine resin in order to prevent water or the like from entering therein has been employed.

When such an oxygen sensor is used for detecting the density of oxygen contained in an exhaust gas at an elevated temperature, the water repellant filter 508 may be deteriorated in gas permeability by heat due to exposure to an elevated temperature after long term use.

In order to solve this problem, as stated in Japanese Patent Laid-Open No.54063/97, a method of forming an air hole on the sealing member provided on the side of the opened end of the cylindrical cover facing toward the outside of the pipe defining a flow path for a gas-to-be-measured, and inserting a bar-shaped filter through the air hole is considered. By disposing the filter in the sealing member, the sealing member is positioned at a distance from the flow path and thus heat is not easily transferred from the pipe defining a flow path. Consequently, the possibility that the filter is exposed to an elevated temperature may be reduced. However, such a bar-shaped filter has a problem in that high resistance is generated when a gas is passed through and thus introduction of the air may be insufficient.

Such a problem occurs not only in an oxygen sensor, but also in gas sensors such as the NOx sensor or the HC sensor that require introduction of air.

SUMMARY OF THE INVENTION

In view of the above, it is therefore an object of the present invention to provide a gas sensor which functions by introducing air from the outside, wherein the property of introducing air may be maintained even when used at an elevated temperature.

Accordingly, a gas sensor according to a general aspect of the present invention comprises a cover including a gas permeable sealing member having an air hole and a gas permeable water repellant filter for closing said air hole, wherein said water repellant filter is formed in a sheet-shape and mounted in said air hole via a cylindrical inserting member that can be inserted into said air hole.

A gas sensor according to a first aspect of the present invention comprises a detecting element having electrodes on first and the second surfaces of an oxygen ion conductive solid-state electrolyte, a main fitting having a fitting portion to be fitted into a mounting hole formed on a wall of a pipe defining a flow path for a gas-to-be-measured for holding said detecting element in such manner that said first surface is disposed via said mounting hole at an inner position of said pipe with respect to said fitting portion, a cylindrical cover of which one end is connected to an outer position of said pipe with respect to the fitting portion of said main fitting and the other end is provided with a cylindrical sealing member having an air hole for introducing air to said second surface on one end and a through hole through which a lead connected to both electrodes of said detecting element passes on the other end, and a water repellant filter having gas permeability for closing said air hole, characterized in that said water repellant filter is formed in a sheet shape and mounted on said air hole by means of a cylindrical inserting member that can be inserted in said air hole.

In the gas sensor according to the first aspect of the present invention, since the water repellant filter is formed in a sheet shape, preferably gas permeability can be obtained. In addition, since the water repellant filter is mounted on the sealing member and thus it is hardly affected by heat, the gas permeability can be maintained even when said gas sensor is exposed to heat from the outside.

According to a second aspect of the invention, in order to fix the water repellant filter described above to the air hole, the water repellant filter is preferably interposed between the outer peripheral surface of the cylindrical inserting member and the inner peripheral surface of said air hole so as to close the opened end of the cylindrical inserting member.

In the gas sensor in this arrangement according to the second aspect of the invention, the water repellant filter can be mounted to the air hole easily by pressing the water repellant filter into the air hole by means of a cylindrical inserting member. It is also possible to cover the opening of the cylindrical inserting member in advance, and then insert the cylindrical inserting member into the air hole.

In the structure according to the second aspect, the water repellant filter is interposed or directly brought into intimate contact between the inner peripheral surface of the air hole and the outer peripheral surface of the cylindrical inserting member so that the sealing property between them is established. Since the opened end of at least one cylindrical inserting member is closed by the water repellant filter, it can prevent passage of water drops through the inside of the cylindrical inserting member, thereby realizing waterproof at the air hole of the sealing member.

Though it is preferable to interpose the water repellant filter between the outer peripheral surface of the cylindrical inserting member and the inner peripheral surface of the air hole because the effects as described above may be obtained as described thus far, there is a possibility that the water repellant filter is displaced. As a consequence, there is a possibility that sufficient waterproof property may not be established at the air hole.

According to a third aspect of the invention, the cylindrical inserting member is preferably provided on its outer peripheral surface at the portion that comes into contact with the water repellant filter with an engaging portion with which the water repellant filter engages when the water repellant filter is interposed between the portion of the outer peripheral surface of the cylindrical inserting member being in contact with the water repellant filter and the inner peripheral surface of the air hole.

In the gas sensor in this arrangement according to the third aspect of the invention, since the water repellant filter is positively retained by the engaging portion when being interposed between the outer peripheral surface of the cylindrical inserting member and the inner peripheral surface of the air hole, displacement caused by shrinkage of the water repellant filter itself under the environment of an elevated temperature, or expansion and shrinkage of the sealing member due to thermal cycle does not occur easily, thereby increasing reliability of the water proof property.

An engaging portion may be constructed as a through hole formed on the side surface of the cylindrical inserting member or a dented hole formed on the outer peripheral surface of the cylindrical inserting member. Since the sealing member is resilient, the water repellant filter is forced into the hole portion by being pressed by the sealing member and thus the water repellant filter is engaged.

An engaging portion may also be constructed as a projection protruding from the outer peripheral surface of the cylindrical inserting member outwardly. The water repellant filter is then forced into and engaged with the sealing member by being pressed by said projection.

In the structure according to the second and third aspects of the invention, it is preferable to arrange the water repellant filter in such manner that the edge thereof can be visually observed as in the fourth aspect of the invention. In this arrangement, an inspection can be made to determine whether or not the water repellant filter is stably interposed between the outer peripheral surface of the cylindrical inserting member and the inner peripheral surface of the air hole.

According to a fifth aspect of the invention, it is also possible to interpose the water repellant filter between the inner peripheral surface of the outer fitting member that can be fitted on the outer peripheral surface of the cylindrical inserting member and the outer peripheral surface of the cylindrical inserting member.

In the gas sensor according to the fifth aspect of the invention, for example, the water repellant filter can be disposed at the air hole by a procedure comprising the steps of fixing the water repellant filter on the cylindrical inserting member in advance (with the opened end of the cylindrical inserting member closed), and inserting this cylindrical inserting member into the air hole of the sealing member. In other words, the cylindrical inserting member and the water repellant filter can be handled as a unit. Therefore, for example, an inspection can be made to determine whether or not the water repellant filter is positively closing the opened end of the cylindrical inserting member in the stage where the cylindrical inserting member is assembled as a unit. As a consequence, nonconformity of waterproofing can be discovered in the early stage of assembly, thereby reducing production cost.

According to a sixth aspect of the invention, it is preferable that the water repellant filter is interposed between the outer peripheral surface of opened end of the cylindrical inserting member closed by said water repellant filter and the inner peripheral surface of the outer fitting member In this arrangement, since the water repellant filter is clamped by the outer peripheral surface of the opened end to be closed, the area of the water repellant filter required to close the opened end of the cylindrical inserting member (and thus the air hole of the sealing member) may be reduced, thereby reducing the cost required for manufacturing the water repellant filter.

According to a seventh aspect of the invention, it is preferable that the outer peripheral surface of the cylindrical inserting member is provided with a limiting portion for limiting the movement of the outer fitting member along the axis of the cylindrical inserting member. According to the gas sensor in this arrangement, positioning of the outer fitting member on the outer peripheral surface of the cylindrical inserting member can be made easily, thereby facilitating assembly. Displacement of the water repellant filter can be prevented as well.

The limiting portion may be constructed as a projection (for example, a flange-shaped projection) protruding outwardly from the outer peripheral surface of the cylindrical inserting member, or as a shoulder in which the thickness of the cylindrical inserting member changes in the direction of the axis.

According to an eighth aspect of the invention, it is preferable that the outer fitting member and the cylindrical inserting member (not limited to the limiting portion) are directly and partly in contact with respect to each other. In the portion where both members are in direct contact with respect to each other (in other words, the portion where the water repellant filer is not interposed), both members can be joined without damaging the water repellant filter by providing a projection and a depression that can be fitted with respect to each other or by crimping, thereby ensuring that the outer fitting member is fixed to the cylindrical inserting member.

In the gas sensor according to the fifth to eighth aspects of the invention, fixing the water repellant filer to the cylindrical inserting member in such a manner that the edge thereof can be visually observed as in the ninth aspect of the invention enables the user to inspect whether or not the water repellant filer is stably interposed between the outer peripheral surface of the cylindrical inserting member and the inner peripheral surface of the outer fitting portion.

According to a tenth aspect of the invention, the part of the outer peripheral surface of the cylindrical inserting member coming into contact with the water repellant filter is preferably roughened. This arrangement ensures that the water repellant filter is more positively retained on the outer peripheral surface of the cylindrical inserting member.

According to an eleventh aspect of the invention, it is preferable to provide the portion of the outer peripheral surface of the cylindrical inserting member that comes into contact with the water repellant filter with a tapered portion that tapers in a direction away from the opened end that is closed by the water repellent filter. In this arrangement, the water repellant filter is pulled in the direction away from the opened end to be closed, whereby the water repellant filter closes the opened end of the cylindrical inserting member more reliably.

According to a twelfth aspect of the invention, the opened end of the cylindrical inserting member closed by the water repellant filter preferably projects from the opened end of the air hole facing toward the outer portion of said gas sensor. In this arrangement, even when a liquid such as water or oil is trapped in the vicinity of the opened end of the air hole facing toward the outside of said gas sensor, the water repellant filter that closes the open end of the cylindrical inserting member is prevented from being covered by a liquid.

The water repellant filter may be constructed by a porous fiber structure formed, for example, of polytetrafluoroethylene (PTFE). However, when manufacturing such a filter into a sheet-shape by drawing it in a certain direction, the resultant fiber structure exhibits a property to be more likely to stretch in the direction orthogonal to that direction. Such a structure may have a property of shrinking in one direction when heated. In addition, when interposing the water repellant filter between the inner peripheral surface of the air hole or the outer fitting member and the outer peripheral surface of the cylindrical inserting member, the filter may be fixed in the state of being stretched. For example, when inserting the filter into the air hole in the state of covering the cylindrical inserting member, a frictional force between the filter and the inner surface of the air hole stretches the filter. However since the stretching property of the filter differs depending on the direction, it stretches in the stretching direction and accordingly it shrinks in the direction orthogonal to the stretching direction, and thus it is difficult to insert uniformly. There may be a case where the length of the filter is long enough for being interposed in one direction, but is too short to be interposed in the other direction thereby making it difficult to be stably interpose the filter.

Therefore, according to a thirteenth aspect of the present invention, in the case where the water repellant filter has an anisotropic property in the extent of shrinkage when heated or when inserted, the filter may be formed longer in the direction in which it is apt to shrink in advance. In this arrangement, even when shrinkage occurs upon heating, the water repellant filter can be retained between the inner peripheral surface of the air hole or the outer fitting member and the cylindrical inserting member. As a detailed configuration of the filter, an oval shaped filter having a longer axis in the shrinking direction and a shorter axis in the stretching direction as stated in the fourteenth aspect of the invention may be employed. The oval figure resists exhibiting a directional property as described above, so that the water repellant filter is uniformly held between the cylindrical inserting member and the sealing member. The configuration of the filter is not limited to an oval figure, and the configuration having a longer axis and a shorter axis such as a rectangular shape may also be employed.

As stated in a fifteenth aspect of the invention, it is preferable to form the air hole coaxially with the sealing member, and to form the cylindrical inserting member with a material harder than the sealing member.

In the gas sensor having such an arrangement according to the fifteenth embodiment of the invention, unevenness of a stress generated inside the sealing member by a crimping operation may be prevented, thereby improving the sealing property due to the sealing member. Any material may be employed for the cylindrical inserting member as long as it is capable of resisting an external force, and metals such as SUS 304 or a resin such as PTFE are preferable.

According to a sixteenth aspect of the present invention, it is preferable to provide a flange that engages with the sealing member on the outer peripheral surface of the cylindrical inserting member.

According to a gas sensor in this arrangement as set forth in the sixteenth aspect of the invention, the flange provided on the outer peripheral surface of the cylindrical inserting member preferably engages the sealing member, thereby resisting detachment of the cylindrical inserting member from the air hole.

In the gas sensor according to the sixteenth aspect of the invention, the flange of the cylindrical inserting member may be constructed to engage any portion of the sealing member. For example, though the flange may be constructed so as to engage the outer peripheral surface around the opening of the air hole, a part of the cylindrical inserting member may overhang out of the air hole and may result in limiting the layout of other parts by narrowing the space therearound.

Therefore, the flange is preferably constructed to engage the engaging portion formed in the air hole according to a seventeenth aspect of the invention.

In the gas sensor according to the seventeenth aspect, since the flange engages with the engaging portion formed in the air hole, it does not overhang outside the air hole and thus the space can be used effectively.

According to an eighteenth aspect of the invention, the flange preferably has a notch. In this arrangement, the water repellant filter engages the notch, and thus displacement of the water repellant filter can be prevented. Though the flange may hide the edge of the water repellant filter and thus visual observation cannot be made, it is also possible to enable visual observation through the notch.

According to a nineteenth aspect of the invention, a water repellant filter having an oil repellant property is preferably used. In this arrangement, the water repellant filter prevents oil from attaching thereon, thereby ensuring gas permeability of the air hole.

According to a twentieth aspect of the invention, in order to positively prevent passage of liquid such as water drops or oil through the air hole, two pieces of the water repellant filters are preferably provided in the direction of the axis of the air hole.

According to a twenty-first aspect of the invention, forming the outer surface of the sealing member facing toward the outside of said gas sensor into a convex shape preferably prevents the outer surface from trapping or being covered by liquid.

According to a twenty-second aspect of the invention, the convex shape of the outer surface of the sealing member is preferably formed so as to be highest at the opened end of the air hole facing toward the outside of said gas sensor to prevent gas permeability from becoming deteriorated due to more efficient attachment of liquid on the water repellant filter.

According to a twenty-third aspect of the invention, the water repellant filter may be adhered and fixed on its periphery directly to the opened end of the cylindrical inserting member. In this case, though troublesome work to adhere the outer peripheral edge of the water repellant filter to the opened end of the cylindrical inserting member is required, the amount of the costly water repellant filters to be used may be reduced.

BRIEF DESCRIPTION OF THE DRAWINGS

FIG. 3 is an explanatory drawing showing the structure of the sealing member and the cylindrical inserting member according to the first embodiment.

FIG. 10(a)–FIG. 10(f) are explanatory drawings showing an alternative of the cylindrical inserting member;

DESCRIPTION OF THE PREFERRED EMBODIMENTS

Figure 1:
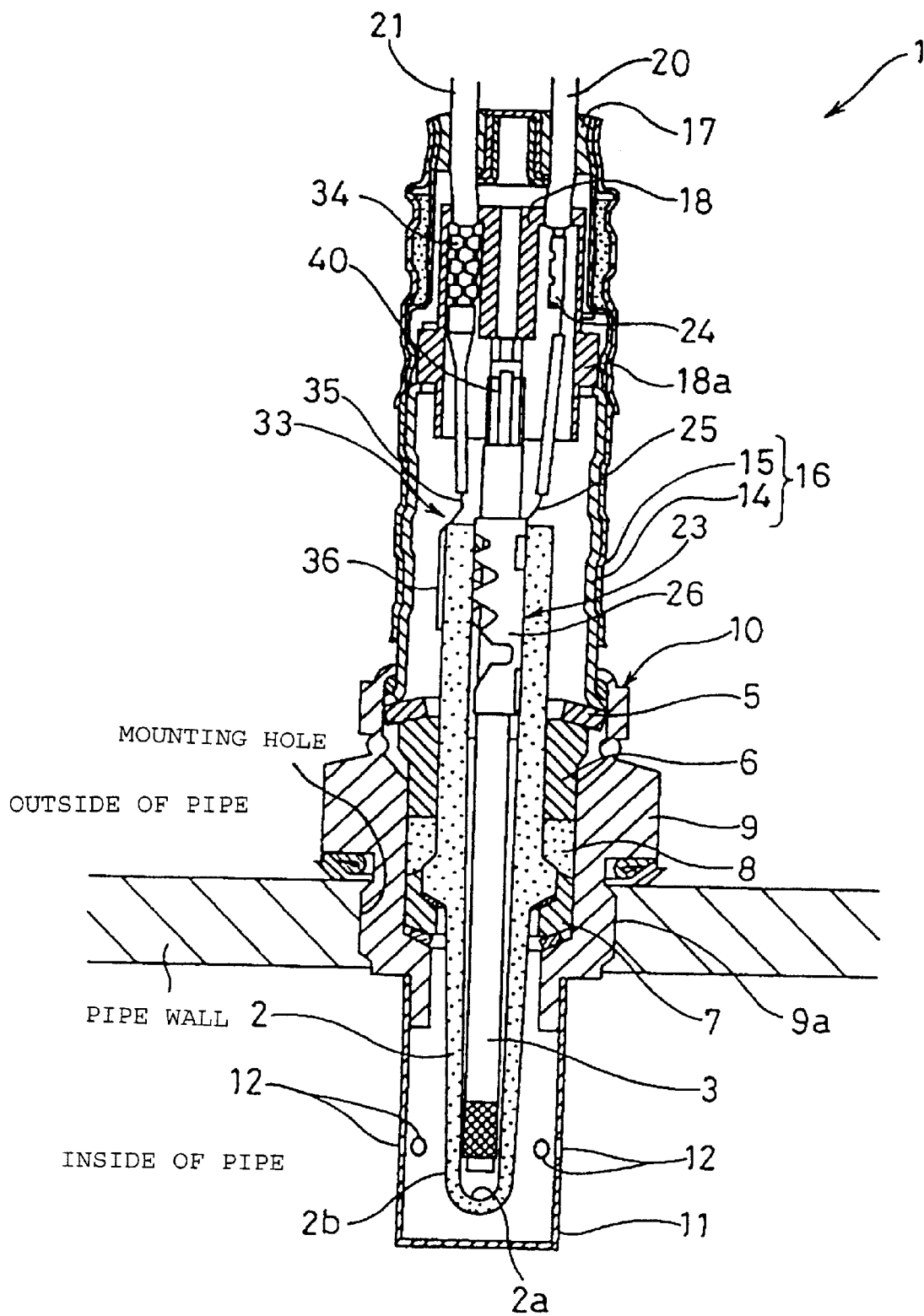
FIG. 1 is a cross sectional view showing the whole structure of an oxygen sensor according to a first embodiment.

Referring now to the drawings, an embodiment of the present invention will be described. FIG. 1 is a cross sectional view showing the whole structure of an oxygen sensor according to a first embodiment.

As shown in FIG. 1, the oxygen sensor 1 of the first embodiment comprises a detecting element 2 formed of a solid-state electrolyte containing $ZrO_2$ as a main component into a hollow shaft having a closed tip portion, a shaft-shaped ceramic heater 3 arranged in the detecting element 2, and a casing 10 for accommodating the detecting element 2.

The detecting element 2 is fixed in the metallic casing 10 around the outer periphery near the mid section in the direction of the axis via ceramic holders 6, 7 formed of insulating ceramic and ceramic powder 8 formed of talc in the stated of being insulated. A pair of porous electrode layers formed of Pt (internal electrode 2a, external electrode 2b) are provided on the inner surface and the outer surface of the detecting element 2 so as to cover whole surface thereof. The outer surface and the inner surface of the detecting element 2 correspond to the first and second surfaces respectively.

The casing 10 comprises a main fitting 9 for fixing the oxygen sensor 1 to the fitting portion such as an exhaust pipe so that the closed tip portion of the detecting element 2 projects into the exhaust pipe or the like, and a cylindrical cover 16 extending from the opening of the main fitting 9 toward the outside of the exhaust pipe or the like for introducing air into the inner surface of the detecting element 2. The cylindrical cover 16 comprises a first outer cylinder 14 connected to one of the openings of the main fitting 9 so that the insides thereof are communicated with respect to each other, and a cylindrical second outer cylinder 15 for fitting on said first outer cylinder 14 from above (in other words, in the direction from the outside toward the exhaust pipe of the like to which the oxygen sensor 1 is mounted). The first outer cylinder 14 and the second outer cylinder 15 correspond to the first cover and the second cover respectively.

On the lower part of the main fitting 9 (in other words, within the exhaust pipe or the like to which the oxygen sensor 1 is mounted), a protector 11 is provided so as to cover the tip portion of the detecting element 2 at a certain space, and the protector 11 is formed with a plurality of gas passages 12 for allowing the exhaust gas to pass through.

On the upper opening of the main fitting 9, the lower opened end of the first outer cylinder 14 is fixed by crimping via a ring 5 between itself and the ceramic holder 6, so that the first outer cylinder 14 extends from the upper opening of the main fitting 9. On the other hand, in the upper opening of the first outer cylinder 14, an insulating separator 18 is provided formed of ceramic in a cylindrical shape. A flange 18a is provided around the outer peripheral surface of the separator 18 so that the separator 18 is held in the upper opening of the first outer cylinder 14 by engagement between the flange 18a and the upper opening edge of the first outer cylinder 14. From above the separator 18, the second outer cylinder 15 is provided and fitted on said first outer cylinder 14.

In the upper opening of the second outer cylinder 15, there is provided a cylindrical rubber sealing member 17, and a pair of leads 20, 21 to be connected to the electrodes of the detecting element 2 respectively and a pair of leads (not shown) to be connected to the ceramic heater 3 so as to pass through the sealing member 17 and the separator 18.

One of the leads 20 for the detecting element 2 is electrically connected to the inner electrode 2a of the detecting element 2 via a terminal fitting 23 composed of a connector portion 24, a leader line portion 25 and the inner electrode connecting portion 26. The other lead 21 is electrically connected to the outer electrode 2b of the detecting element 2 via a terminal fitting 33 composed of a connector portion 34, a leader line portion 35, and the external electrode connecting portion 36.

A pair of heater terminals 40 for energizing the ceramic heater 3 are fixed on the upper end of the ceramic heater 3, so that the exoergic resistance circuit (not shown) embedded within the ceramic heater 3 is energized via these heater terminals 40.

Figure 2:
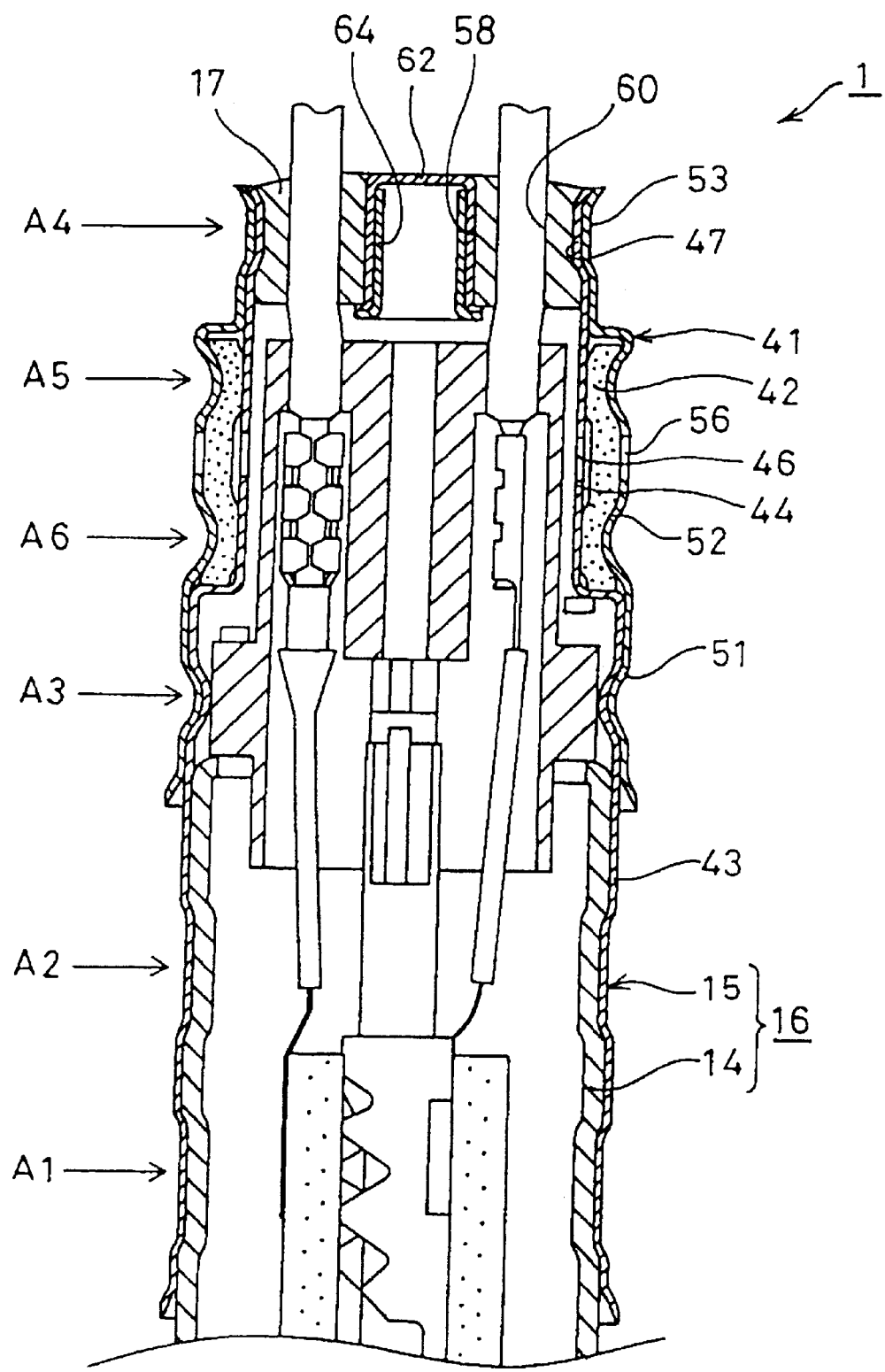
FIG. 2 is an explanatory drawing showing the structure in the vicinity of the cylindrical cover according to the first embodiment.

As shown in FIG. 2, air ventilation of the inner space of the first outer cylinder 14 and the second outer cylinder 15 in the oxygen sensor 1 of the first embodiment is carried out through the first water repellant filter 42 disposed between the second outer cylinder 15 and the protective outer cylinder 41 fitted on the second outer cylinder 15 and the second water repellant filter 62 provided in the sealing member 17. The second water repellant filter 62 corresponds to the water repellant filter stated in the appended claims.

The mounting structure of the first water repellant filter 42 and the second water repellant filter 62 will now be described.

The second outer cylinder 15 is, as described above, connected with the upper portion of the first outer cylinder 14 (in other words, opposite side of the first outer cylinder 14 from the main fitting 9), and the inside thereof is in communication with the inside of the first outer cylinder 14. The second outer cylinder 15 comprises a cylindrical large diameter section 43 fixed on the first outer cylinder 14 by radially crimping (position A1, A2) from the lower portion (from the side of the main fitting 9), a cylindrical air hole defining section 44 having a first air hole 46 and fitted with the first water repellant filter 42 thereon, and an opened end 47 for fitting on the cylindrical sealing member 17.

On the other hand, the protective outer cylinder 41 is formed so as to be able to fit on the upper structure (upper portion of the large diameter section 43, the air hole defining section 44, and the opened end 47) of the second outer cylinder 15. More specifically, the protective outer cylinder 41 comprises, from the lower side, a large diameter section 51 fitted and overlaid on the large diameter section 43 of the second outer cylinder 15, a cylindrical filter protecting section 52 covering the outer periphery of the first water repellant filter 42 fitted on the air hole defining section 44 of the second outer cylinder 15, and a small diameter section 53 fitted on the opened end 47 of the second outer cylinder 15.

The protective outer cylinder 41 is radially crimped (position A3) by the large diameter portion 51 overlying on the large diameter section 43 of the second outer cylinder 15, and radially crimped (position A4) by the small diameter section 53 overlying on the opened end 47 of the second outer cylinder 15 and thereby fixed to the second outer cylinder 15. The sealing member 17 is fixed on the inner surface of the opened end 47 of the second outer cylinder 15 by being crimped at the small diameter section 53 (position A4) so that sealing between the inner peripheral surface of the second outer cylinder 15 and the outer peripheral surface of the sealing member 17 is established.

The first water repellant filter 42 is of a sheet type formed in a cylindrical shape, and arranged in the space formed between the air hole defining section 44 and the filter-protecting portion 52 of the protective outer cylinder 41. The first water repellant filter 42 is constructed as a water repellant filter that prevents passage of liquid mainly composed of water such as water drops and allows passage of gas (air, water vapor) by a porous fiber structure (for example, trade name: GORE-TEX (JAPAN GORE-TEX Inc.)) obtained by drawing unsintered moldings of polytetrafluoroethylene (PTFE) in directions of more than one axis at a heating temperature lower than the fusion point of the PTFE. It is also possible to employ a porous fiber structure coated with an oil repellant material (trade name: OREO BENT FILTER (JAPAN GORE-TEX Inc.). Employing this structure reduces the possibility that attached oil is vaporized and enters inside.

The filter protecting portion 52 of the protective outer cylinder 41 is radially crimped on the upper side (position A5) and the lower side (position A6) of the first air hole 46 of the second outer cylinder 15, thereby preventing water or the like from entering into the oxygen sensor 1 through the air hole defining section 44 and the first water repellant filter 42. In the filter protecting portion 52, a through hole 56 for introducing air into the first water repellant filter 42 is formed at the position between both crimping positions A5 and A6, in other words, at the position corresponding to the first air hole 46. In this arrangement, gas communication between the inside and the outside of the oxygen sensor 1 is carried out through the first air hole 46, the first water repellant filter 42 and a through hole 56.

The sealing member 17 provided within the opened end 47 of the second outer cylinder 15 comprises, as shown in FIG. 3, a second air hole 58 for allowing a gas to flow between the inside and the outside of the oxygen sensor 1 and insertion holes 60 (at four points corresponding to the number of the lead in the first embodiment) through which the leads (leads 20, 21 for the detecting element 2, and leads for the ceramic heater 3) to be drawn out from the oxygen sensor 1 are passed.

The second air hole 58 is formed coaxially with the sealing member 17, through which the second water repellant filter 62 of a sheet shape formed of said porous fiber structure into a cylindrical shape is inserted via a cylindrical inserting member 64 and fixed therein. The cylindrical inserting member 64 has opened ends and is formed into a cylindrical shape that can be fitted into the second air hole 58. The second water repellant filter 62 is stretched to the size that can cover one of openings 64a of the cylindrical inserting member 64 and the outer surface thereof, and inserted into the second air hole 58 together with the cylindrical inserting member 64 in the state of covering the cylindrical inserting member 64. In this arrangement, the second water repellant filter 62 is interposed between the outer peripheral surface of the cylindrical inserting member 64 and the inner peripheral surface of the second air hole 58, and fixed with the second air hole 58 closed.

On the outer periphery of the opened end of the cylindrical inserting member 64 opposite (lower side in FIG. 3) from the direction of insertion into the second air hole 58 (upper side in FIG. 3), a flange 64b is provided. When the cylindrical inserting member 64 is inserted from below the second air hole 58, the flange 64b is stopped at the lower opened edge of the second air hole 58, whereby the cylindrical inserting member 64 and the second water repellant filter 62 are positioned in the second air hole 58.

When the sealing member 17 is disposed inside the opened end 47 of the second outer cylinder 15, and radially crimped via the second outer cylinder and the protective outer cylinder 41 (position A4), sealing between the cylindrical inserting member 64 and the sealing member 17 is enhanced.

While the water repellant filter is manufactured by drawing in one direction as described above, there is a type that exhibits an anisotropic property when heated and a type that does not exhibit an anisotropic property when heated. In this embodiment, a filter of the type exhibiting an anisotropic property is used as a second water repellant filter 62. One of the second water repellant filters 62 is obtained by cutting a larger sized porous fiber structure of sheet type into a suitable shape, and thus it is cut into a sufficient length in the direction in which shrinkage may occur due to an anisotropic property.

Though the second water repellant filter 62 may be obtained at low cost as long as it is formed easily by drawing in one direction, the stretching property of the filter manufactured by drawing in one direction is different depending on the direction. In other words, it is apt to stretch in one direction and correspondingly, it is apt to shrink in the direction orthogonal to the stretching direction. Therefore, when the cylindrical inserting member 64 is inserted into the air hole 58 with the second water repelling filter 62 covered thereon, the water repellant filter is pulled in one direction due to a frictional force between the water repellant filer and the inner surface of the air hole. Therefore, when the second water repellant filter 62 is formed in a circular sheet for example, it stretches in one direction and shrinks in the direction orthogonal to the stretching direction, whereby it is difficult to clamp the water repellant filter uniformly between the outer peripheral surface of the cylindrical inserting member 64 and the inner peripheral surface of the air hole 58. As a consequence, especially when the gas sensor is in use, in the case where the water repellant filter is elevated in association with heat expansion of the sealing member, there is an apprehension that the shrunk portion of the elevated water repellant filter comes apart from the air hole 58.

Figure 13:
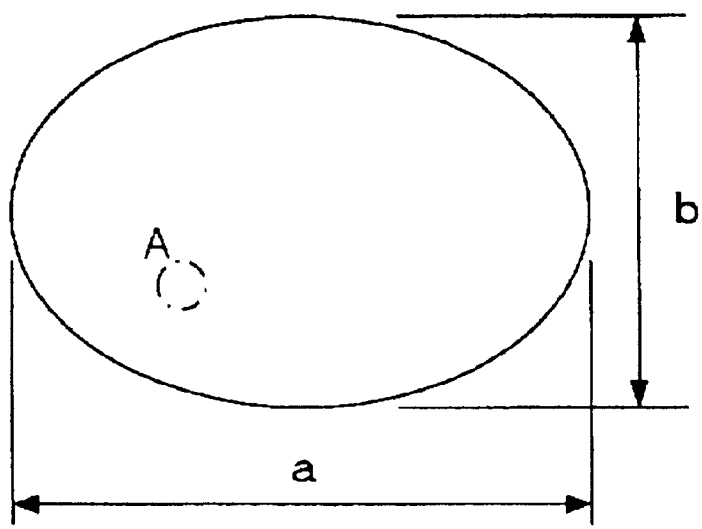
FIG. 13(a) is a configuration of the water repellant filter according to the first embodiment.
FIG. 13(b) is an explanatory drawing showing a microstructure of the water repellant filter, enlarged at a portion A of FIG. 13(a).
Figure 13:
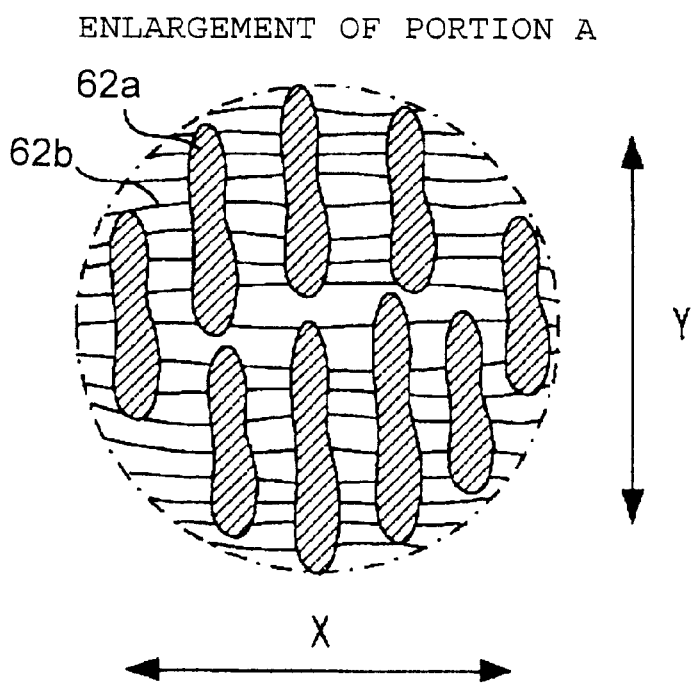

Therefore, in this embodiment, the water repellant filter 62 is formed in an oval shaped sheet of which the length of the longer axis is a and that of the shorter axis is b (a>b), as shown in FIG. 13(a). As shown in FIG. 13(b), which is a partially enlarged view of FIG. 13(a), the repellant filter 62 exhibits an anisotropic property according to microscopic observation. In other words, a plurality of fiber grains 62a are connected by a number of fiber threads 62b. It is because fiber grains 62a are broken up in a stringy state during a one-direction drawing process. Such fibers are hardened in the direction in which the fibers are drawn (direction X: direction of fibers), and thus the stretching property is lowered. In contrast, since the stretching property of such fibers in the direction orthogonal to the direction X (direction Y) is high, it stretches easily while enlarging the intervals between fiber strings. Therefore, the water repellant filter 62 employs an oval shape that is longer in the direction of the fibers and shorter in the direction orthogonal to the direction of the fibers, so that it is deformed into a perfect circle when being stretched. Since the most suitable length of the longer axis a and the length of the shorter axis b vary depending on the depth of the air hole 58 into which the water repellant filter 62 is inserted or the like, the appropriate values are determined depending on the design requirements of the oxygen sensor 1.

In this embodiment, the ratio of the length in the shorter direction to that in the longer direction is set to 7:8. The second water repellant filter 62 is formed in an oval shape with a ratio of the shorter diameter to the longer diameter of about 7:8 so that the second water repellant filter 62 is deformed generally into a circle after shrinkage.

When the oxygen sensor 1 in this arrangement is fitted into the mounting hole of the pipe defining a flow path for a gas-to-be-measured via a screw portion 9a formed on the outer peripheral surface of the main fitting 9 in such manner that the cylindrical cover 16 is facing almost upward, the tip portion of the detecting element 2 protected by the protector 11 projects into the inside of the pipe defining a flow path and is exposed to a gas-to-be-measured. On the other hand, in the detecting element 2, air is introduced through the cylindrical cover 16 by ventilation through the first air hole 46 and the second air hole 58. Since the first air hole 46 and the second air hole 58 are closed by the first water repellant filter 42 and the second water repellant filter 62 respectively being of the sheet type with gas permeability, introduction of the air into the cylindrical cover 16 can be carried out sufficiently and entry of water or the like therein is prevented. As a consequence, a voltage according to the ratio of the density of oxygen in the air and the density of oxygen in a gas-to-be-measured is generated between the internal electrode 2a and the external electrode 2b of the detecting element 2 and transmitted to the outside as detected signals through the leads 20, 21. The screw 9a corresponds to the fitting portion in the appended claims.

The oxygen sensor 1 according to the first embodiment as described above has the following effects as stated in (1) to (6).

(1) Since the second water repellant filter 62 is of a sheet type, satisfactory gas permeability is ensured, and even when the second water repellant filter 62 is subjected to heat from the flow path, since it is fixed in the sealing member 17, it resists being affected by heat and maintains its gas permeability. Therefore, introduction of the air into the cylindrical cover 16 may be positively carried out.

(2) Since the second water repellant filter 62 may be interposed between the outer peripheral surface of the cylindrical inserting member 64 and the inner peripheral surface of the second air hole 58 to fix in the second air hole 58 easily, it preferably saves time and effort in production.

(3) Since the second air hole 58 is formed coaxially with the sealing member 17 and having a cylindrical inserting member 64 formed rigidly of metal inserted therein, non-uniformity of stress generated in the sealing member 17 caused by crimping may be prevented, thereby improving the sealing property of the sealing member 17.

(4) Since a flange 64b is formed on the outer peripheral surface of the cylindrical inserting member 64 and engages the sealing member 17 at the peripheral edge of the opening of the second air hole 58 when the cylindrical inserting member 64 is inserted into the second air hole 58, the cylindrical inserting member 64 is prevented from being detached easily from the second air hole 58.

(5) The second water repellant filter 62 is formed longer in length in the direction in which the second water repellant filter is apt to shrink. Therefore, even when shrinkage occurs, the water repellant filter may be positively maintained between the inner surface of the second air hole 58 and the outer peripheral surface of the cylindrical inserting member 64.

(6) When the porous fiber structure coated with an oil repellant material is used as a second water repellent filter, the possibilty that attached oil is vaporized and enters therein may be reduced.

Figure 4:
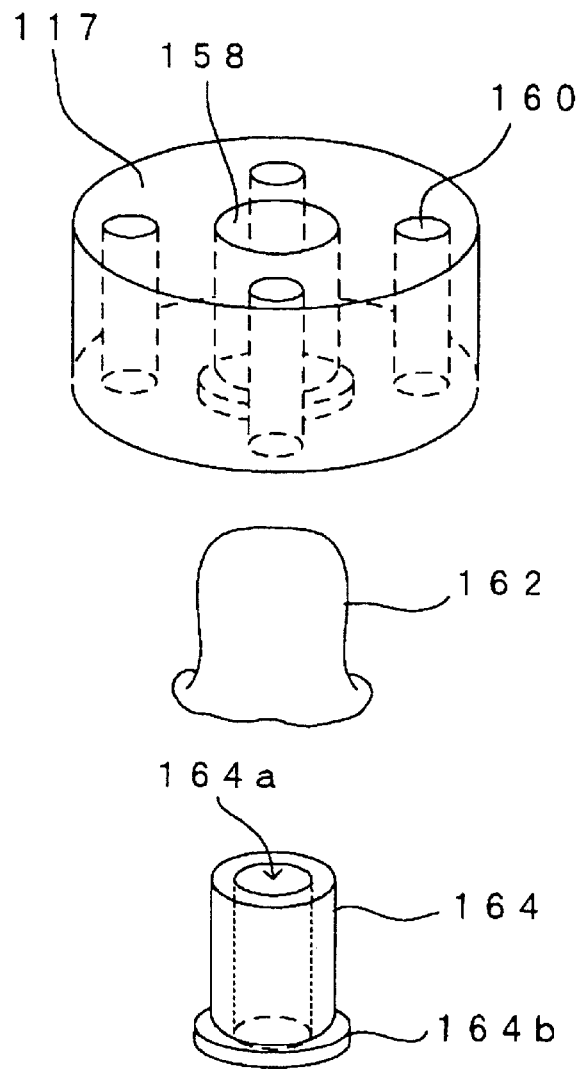
FIG. 4(a) is an explanatory drawing showing the structure of the sealing member and the cylindrical inserting member in the oxygen sensor according to the second embodiment.
FIG. 4(b) is a cross sectional view showing a state in which the cylindrical inserting member is inserted into the second air hole of the sealing member.
Figure 4:
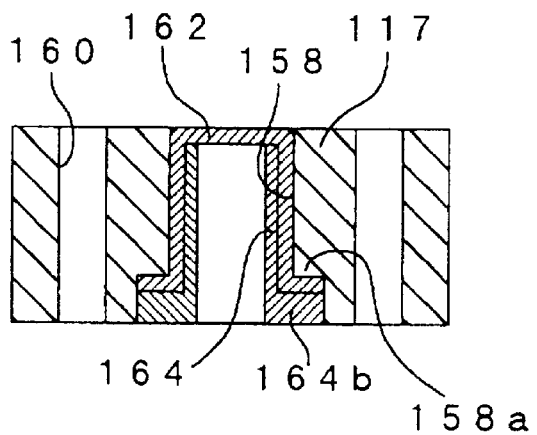

The second embodiment will now be described. FIGS. 4(a) and 4(b) are explanatory drawings showing a sealing member 117 and a cylindrical inserting member 164 in the oxygen sensor of the second embodiment.

The sealing member 117 is formed of rubber and comprises a second air hole 158 for allowing a gas to pass between the inside and the outside of the oxygen sensor 1, and an insertion hole 160 through which the leads to be drawn out from the oxygen sensor 1 are passed. The second air hole 158 formed in the sealing member 117 has an opening through which the flange 164b of the metallic cylindrical inserting member 164 can also be inserted, and is formed with an engaging portion 158a for engaging with the flange 164b. When the second water repellant filter 162 is inserted into the second air hole 158 together with the cylindrical inserting member 164, the flange 164b is engaged with the engaging portion 158a in the second air hole 158, and as a consequence, the cylindrical inserting member 164 and the second water repellant filter 162 are positioned in the second air hole 158.

Other structures are identical to those of the oxygen sensor 1 of the first embodiment, and thus the description will be omitted.

In the oxygen sensor according to the second embodiment as described above, another effect (7) in addition to the effects from (1) to (6) of the first embodiment is expected.

(7) Since the flange 164b of the cylindrical inserting member 164 engages the engaging portion 158a formed in the second air hole 158, it does not overhang out of the second air hole 158, so that the inner space of the oxygen sensor 1 may be effectively utilized.

Figure 5A:
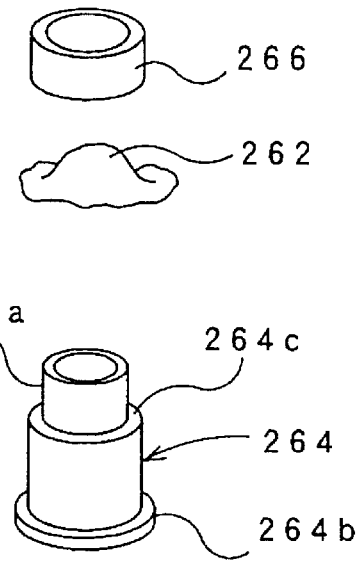
FIG. 5(a) and FIG. 5(b) are explanatory drawings showing the structure in the vicinity of the cylindrical inserting member of the oxygen sensor of the third embodiment.
Figure 5:
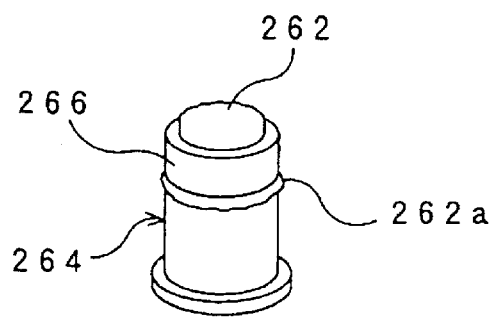
FIG. 5(c) is a cross sectional view showing a state in which the cylindrical inserting member is inserted into the second air hole of the sealing member.
Figure 5:
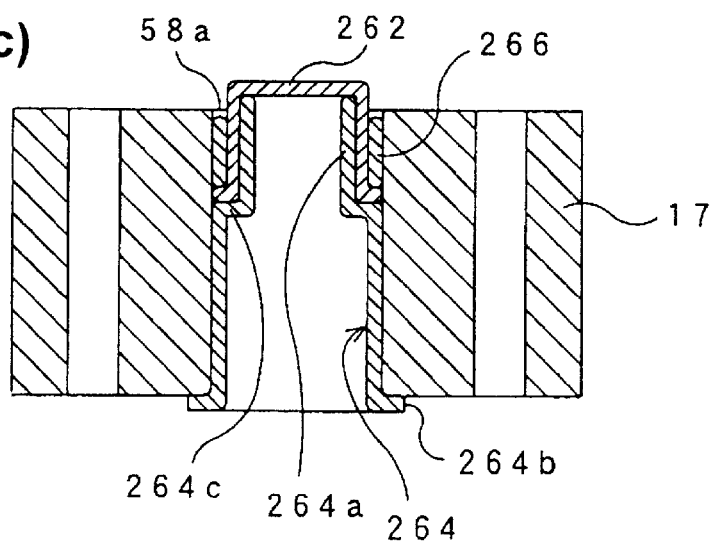

The third embodiment will now be described. FIGS. 5(a), 5(b) and 5(c) are explanatory drawings showing a structure in the vicinity of the air hole 58 of the sealing member 17 in the oxygen sensor according to the third embodiment.

Though the sealing member 17 is the same type as the one in the first embodiment and the second air hole 58 is formed coaxially with the sealing member 17, the second water repellant filter 262 formed of a porous fiber structure of the sheet type is inserted therein via the cylindrical inserting member 264 and fixed as shown in FIG. 5(c).

As shown in FIG. 5(a), the cylindrical inserting member 264 is open on both ends and formed in a cylindrical shape that can be inserted into the second air hole 58. The second water repellant filter 262 has an area so that it can cover the opening of one of the opened ends 264a and the outer peripheral surface of the cylindrical inserting member 264, and is inserted into the outer fitting member 266 together with the cylindrical inserting member 264 with the cylindrical inserting member 264 covered with the second water repellant filter. As a consequence, the second water repellant filter 262 is interposed between the outer peripheral surface of the opened end 264a of the cylindrical inserting member 264 and the inner peripheral surface of the outer fitting member 266 so as to be fixed with the opened end 264a of the cylindrical inserting member 264 which is closed.

In other words, the second water repellent filter 262 is fixed to the cylindrical inserting member 264 by the outer fitting member 266 that can be fitted on the cylindrical inserting member 264 (more specifically, the opened end 264a thereof). The outer fitting member 266 is formed of a metal in cylindrical shape.

The outer peripheral surface of the cylindrical inserting member 264 is provided with a shoulder 264c formed in such manner that the diameter (in other words, the thickness) of the cylindrical inserting member 264 increases from the opened end 264a toward the other opened end. The movement of the outer fitting member 266 along the axis of the cylindrical inserting member 264 is limited by the shoulder 264c when fitted to the opened end 264a of the cylindrical inserting member 264, and as a consequence, the position of the cylindrical inserting member 264 on the outer peripheral surface is determined. The shoulder 264c serves as a limiting portion.

Owing to the cylindrical inserting member 264 and the outer fitting member 266 in such structures, the edge portion 262a of the second water repellant filter 262 fixed on the cylindrical inserting member 264 can be visually observed as shown in FIG. 5(b). In other words, the edge portion 262a of the second water repellant filter 262 is not hidden between the cylindrical inserting member 264 and the outer fitting member 266, but can be seen therebetween. Since the second water repellant filter 262 has also an anisotropic property in shrinkage as in the case of the first embodiment, it is formed longer in the direction in which it is apt to shrink.

The cylindrical inserting member 264 is inserted into the second air hole 58 of the sealing member 17 from the side of the opened end 264a closed by the second water repellant filter 262. In the third embodiment as well, the outer periphery of the opened end on the opposite side (lower side in FIGS. 5(a)–5(c)) from the direction to be inserted into the second air hole 58 is formed with a flange 264b as in the embodiment described above. In other words, a flange 264b is provided on the outer periphery of the opened end opposite from the opened end 264a closed by the second water repellant filter 262.

When the cylindrical inserting member 264 is inserted into the second air hole 58 from below the air hole, the flange 264b is stopped at the lower opened end of the second air hole 58 and as a consequence, the cylindrical inserting member 264 and the second water repellant filter 262 are positioned in the second air hole 58.

The upper opened end 58a of the second air hole 58 faces toward the outside of the oxygen sensor 1. The opened end 264a of the cylindrical inserting member 264 closed by the second water repellant filer 262 projects from the upper opened end 58a of the second air hole 58 when the cylindrical inserting member 264 is positioned in the second air hole 58.

In this way, when the second water repellant filter 262 is provided in the second air hole 58, the second air hole 58 is closed by the second water repellant filter 262. In other words, the outer peripheral surface of the opened end 264a of the cylindrical inserting member 264 and the second water repellant filter 262 covering the opened end 264a come into intimate contact with each other, and thus passage of liquid through the opened end 264a is prevented. In addition, the inner peripheral surface of the second air hole 58 and the outer peripheral surface of the cylindrical inserting member 264 come into intimate contact with each other, and thus passage of liquid therebetween is prevented.

When the sealing member 17 is arranged inside the opened end 47 of the second outer cylinder 15, and radially crimped via the second outer cylinder and the protecting outer cylinder 41 (position A4), sealing between the cylindrical inserting member 264 and the sealing member 17 is enhanced.

Figure 6:
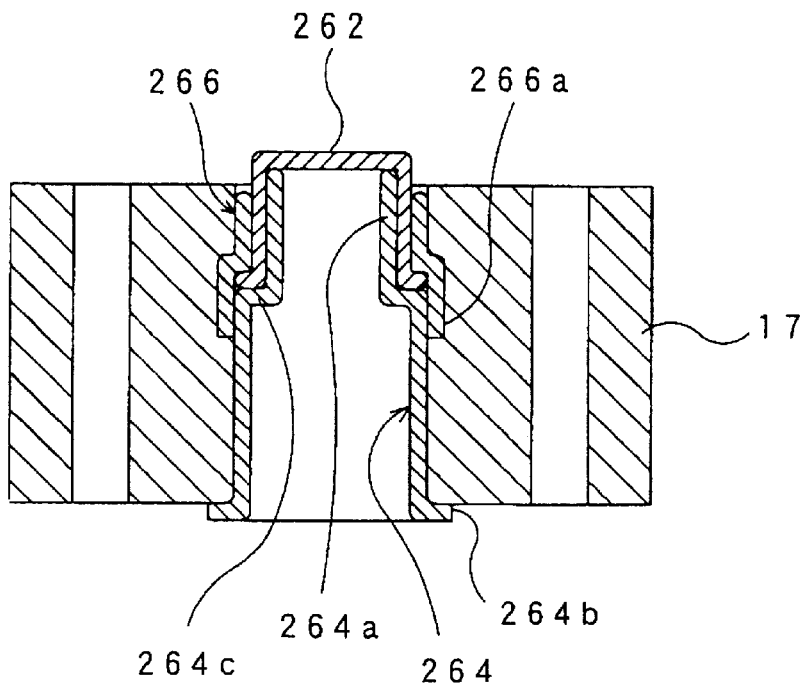
FIG. 6 is an explanatory drawing showing an alternative of the outer fitting member of the third embodiment.

As shown in FIG. 6, the outer fitting member 266 and the cylindrical inserting member 264 are preferably arranged so as to come into partially contact with respect to each other. FIG. 6 shows a state in which the end 266a of the outer fitting member 266 is brought into direct contact with the outer peripheral surface of the cylindrical inserting member 264. In this case, when the end portion 266a of the outer fitting member 266 is simply formed in a cylindrical shape, the edge 262a of the second water repellant filter 262 cannot be visually observed. In order to avoid this, for example, a notch or a through hole is preferably formed at the end portion 266a.

Since other structures are identical to the oxygen sensor 1 of the first embodiment, description will be omitted.

The gas sensor of the third embodiment described above has following effects from (8) to (12) in addition to the effects (1) and (3) to (6) described above.

(8) The cylindrical inserting member 264 and the second water repellant filer 262 can be treated as one unit. Therefore, whether or not the second water repellant filter 262 covers the opened end 64a of the cylindrical inserting member 264 completely can be visually observed in the stage hen the cylindrical inserting member 264 and the second water repellant filter 262 are assembled into one unit. In other words, insufficient waterproofing property can be found in the early stage of assembly, thereby reducing production cost.

(9) The second water repellant filer 262 is interposed between the outer peripheral surface of the opened end 264a closed by the second water repellant filter 262 and the inner peripheral surface of the outer fitting member 266. Therefore, the amount of the second water repellant filter 262 required to close the opened end 264a of the cylindrical inserting member 264 (and thus the second air hole 58 of the sealing member 17) may be reduced, thereby reducing cost.

(10) The outer peripheral surface of the cylindrical inserting member 264 is provided with a shoulder 264c, which limits movement of the outer fitting member 266 along the axis of the cylindrical inserting member 264. Therefore, positioning of the outer fitting member 266 on the outer peripheral surface of the cylindrical inserting member 264 may be effected easily. In addition, since the displacement of the outer fitting member 266 may be restrained, that of the second water repellant filter 262 may be restrained.

(11) The opened end 264a of the cylindrical inserting member 264 closed by the second water repellant filter 262 is projecting from the opened end 58a of the air hole 58 facing toward the outside of the oxygen sensor 1. Therefore, even when liquid such as water or oil is trapped in the vicinity of the opened end 58a of the air hole 58, the second water repellant filer 262 closing the opened end 264a of the cylindrical inserting member 264 is prevented from being covered by liquid, thereby ensuring air permeability thereof.

(12) Since the outer fitting member 266 and the cylindrical inserting member 264 partially come into direct contact with each other, both members are positively connected while clamping the second water repellant filter 262 without damaging it.

Though an embodiment of the present invention has been described thus far, the present invention is not limited thereto, but may be otherwise variously embodied.

For example, though an oxygen sensor is taken as an example of a gas sensor in the embodiment described above, it is not limited thereto, and the present invention may be applied, for example, to an NOx (nitrogen oxides) sensor or a CH (hydrocarbon) sensor.

Though the cylindrical inserting members 64, 164, and 264 are formed of metal in the embodiment described above, they are not limited thereto. In other words, since the cylindrical inserting members 64, 164, 264 are disposed within the sealing members 17, 117 and thus they are hardly affected by heat, it is not necessary to form them of a material having the same heat resistance as metal. For example, the cylindrical inserting members 64, 164, 264 can be formed of ceramic or hard resin, or a highly resilient material such as rubber.

Though the cylindrical inserting member is cylindrical in the embodiment described above, it is not limited thereto.

Though a sheet of the water repellant filter covering the air hole of the sealing member is mounted in the embodiment described above, it is not limited thereto, but a plurality of sheets of filter may be mounted, so that water resistance of the air hole of the sealing member is further enhanced.

Figure 7:
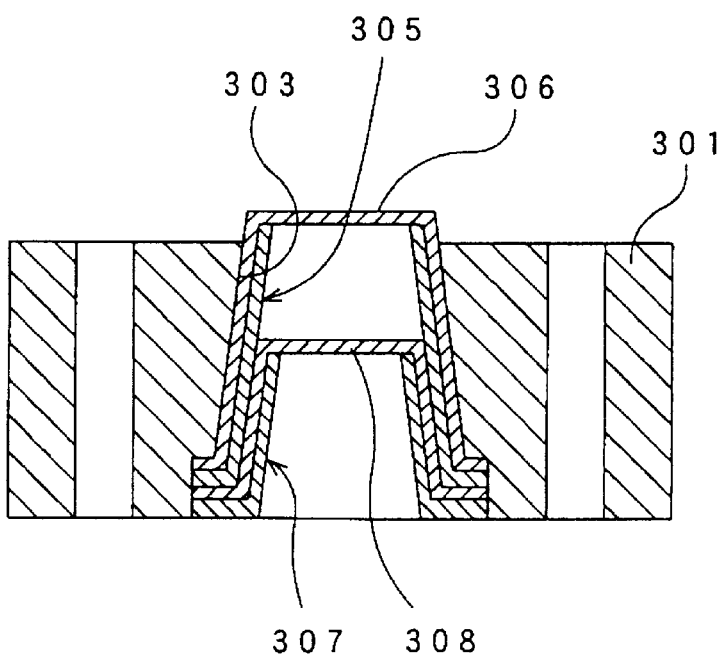
FIG. 7 is an explanatory drawing showing an alternative of the structure in the vicinity of the air hole.

In order to realize this, a plurality of water repellant filters can be simply overlaid one on another. However, since the overlaid water repellant filters are bulky, and thus may be crinkled, the waterproofing property may be hindered. Therefore, a structure, for example, as shown in FIG. 7 may be implemented. In other words, a cylindrical first inserting member 305 insertable into the air hole 303 of the sealing member 301 and a second inserting member 307 insertable into the cylinder of the first inserting member 305 are provided as cylindrical inserting members. The first inserting member 305 is covered on its opened end by the water repellant filter 306, and inserted into the air hole 303 from the covered end side. The water repellant filter 306 is thereby interposed between the inner peripheral surface of the air hole 303 and the outer peripheral surface of the first inserting member 305.

On the other hand, the second inserting member 307 is covered on its opened end by another water repellant filter 308 and inserted into the first inserting member 305 from the covered end side. The water repellant filter 308 is thereby interposed between the outer peripheral surface of the second inserting member 307 and the inner peripheral surface of the first inserting member 305. In this way, a plurality of water repellant filters may be provided at the air hole of the sealing member.

In this case, each cylindrical inserting member (the first inserting member 305 or the second inserting member 307, etc.) is preferably formed into a tapered shape, so that they can easily be combined. In order to close the opened ends of the first and second inserting members 305, 307 by the water repellant filters 306, 308, the outer fitting member such as the third embodiment may be used. It is also possible to provide a water repellant filter on both opened ends of the cylindrical inserting member by the use of an outer fitting member.

Figure 8:
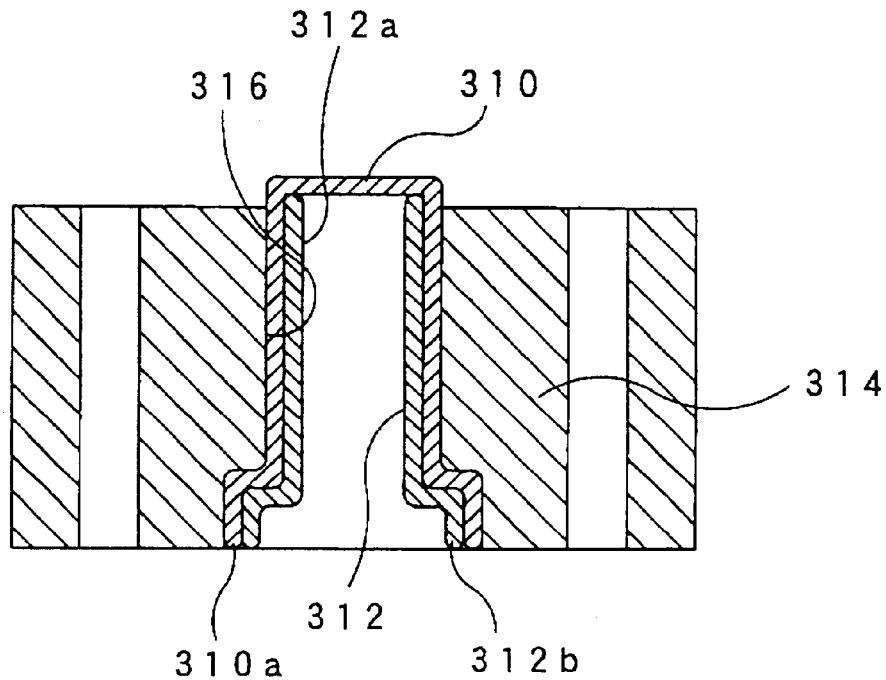
FIG. 8(a) and FIG. 8(b) are explanatory drawings showing an alternative of the structure in the vicinity of the air hole.
Figure 8:
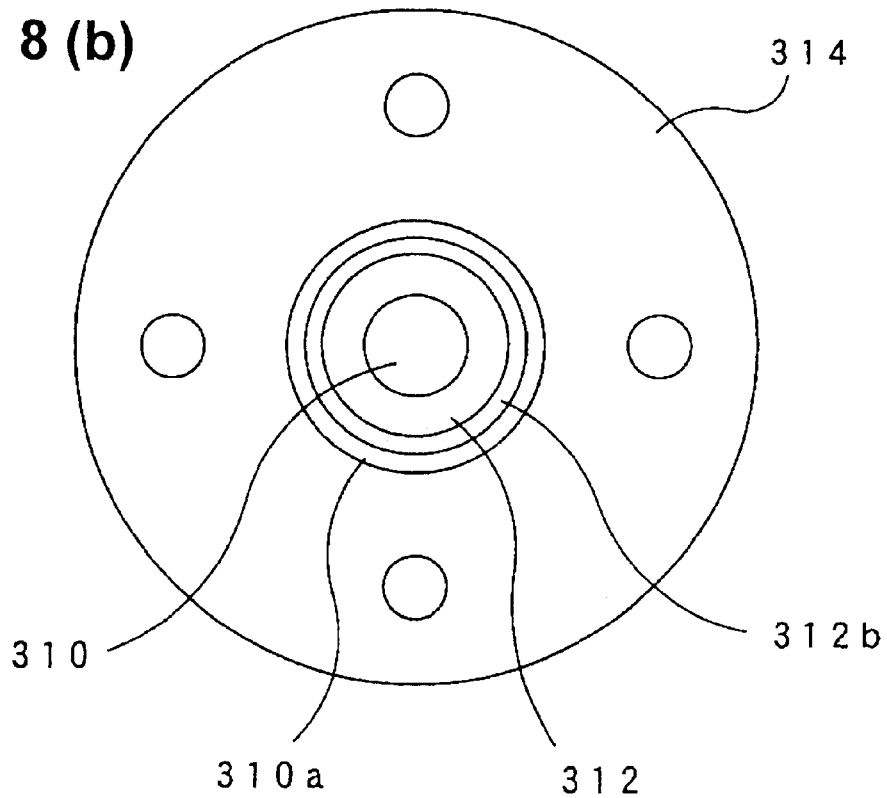

Though the edge of the water repellant filter provided on the air hole of the sealing member may be hidden by interposing between the outer peripheral surface of the cylindrical inserting member and the inner peripheral surface of the air hole, it is preferable to dispose it so as to be visually observed from the outside as shown in FIGS. 8(a) and 8(b) for example.

As shown in FIG. 8(a), the water repellant filter 310 is interposed between the outer peripheral surface of the cylindrical inserting member 312 and the inner peripheral surface of the air hole 316 of the sealing member 314 so as to close the opened end 312a of the cylindrical inserting member 312, and simultaneously covers whole part of the outer peripheral surface of the cylindrical inserting member 312. The edge portion 310a of the water repellant filter 310 reaches the opened end 312b (of the cylindrical inserting member 312) on the opposite side of the closed opened end 312a closed by the water repellant filter 310. The opened end 312b on the opposite side is formed as a flange. The water repellant filter 310 also covers the opened end (flange) 312b, and the edge portion 310a thereof is exposed toward the outside (the bottom of the sealing member 314). FIG. 8(b) is a drawing of the sealing member 314 when viewed from below.

In this way, it is preferable to allow the edge 310a of the water repellant filter 310 to be visually observed because the water repellant filter 310 can be inspected whether or not it is stably interposed between the sealing member 314 and the cylindrical inserting member 312, or whether or not it is not likely to be displaced or detached.

Figure 9:
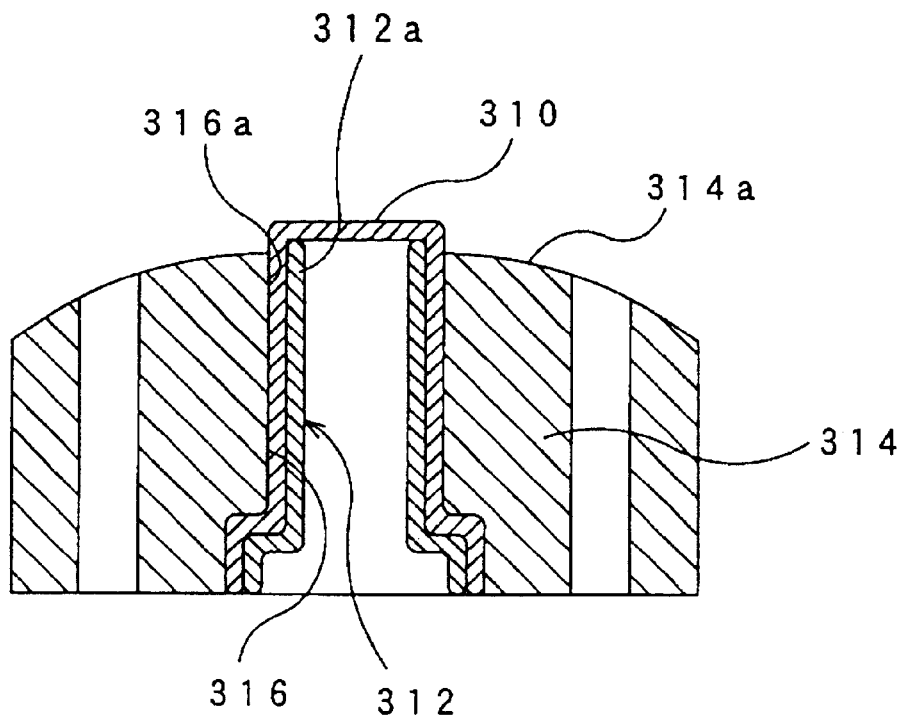
FIG. 9(a) and FIG. 9(b) are explanatory drawings showing an alternative of the sealing member.
Figure 9:
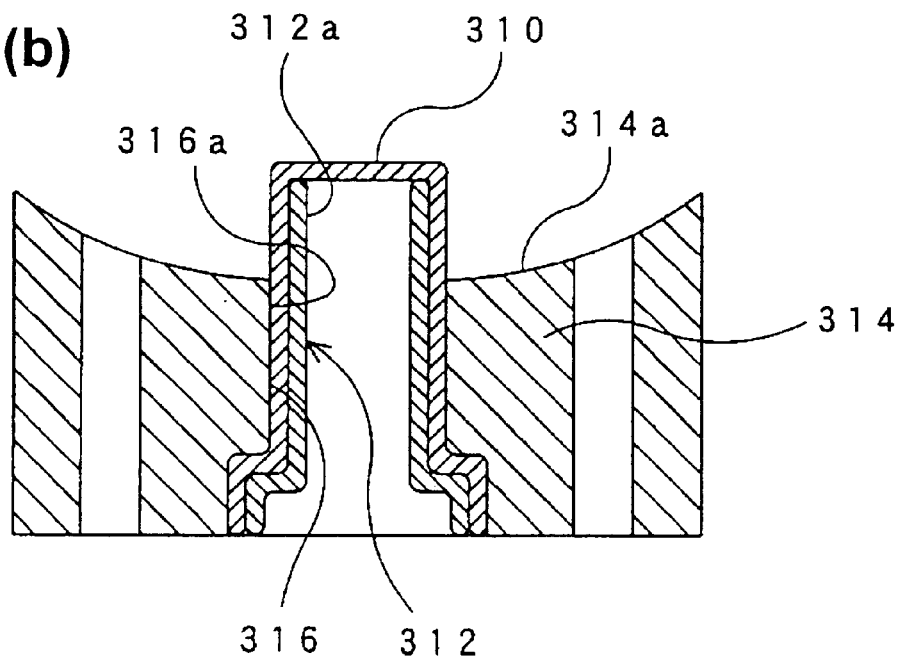

According to the description regarding the third embodiment, the opened end 264a closed by the second water repellant filter 262 of the cylindrical inserting member 264 projects from the opened end 58a of the air hole 58 toward the oxygen sensor 1. In this case, the outer surface (the surface facing toward the outside of the oxygen sensor) of the sealing member may be formed in an approximately flat shape, or may be formed in a concaved shape dented toward the inside of the oxygen sensor 1 as the outer surface 314a of the sealing member 314 as shown in FIG. 9(b). Anyway, the effect (11) can be achieved by simply allowing the opened end 312a closed by the water repellant filter 310 of the cylindrical inserting member 312 to project from the opened end 316a of the air hole 316.

In order to prevent liquid such as water drops from depositing on the water repellant filter, the outer surface 314a of the sealing member 314 is formed in a convex shape as shown in FIG. 9(a). In this arrangement, even when liquid is attached to the outer surface 314a, it is apt to drain down. In other words, the convex shape resists trapping liquid on the outer surface 314a thereof, and thus prevents liquid from deteriorating air permeability by covering the water repellant filter 310. In order to enhance this effect, as shown in FIG. 9(a), the outer surface 314a is preferably formed so that the outer surface 314a projects (swells) most at the opened end 316a of the air hole 316 facing toward the outer portion of the oxygen sensor.

Measures to prevent the water repellant filter from being displaced on the outer peripheral surface of the cylindrical inserting member are shown in FIG. 10(a) to FIG. 10(f) as examples.

FIG. 10(a) is a drawing of the case where a through hole 320a is formed on the outer peripheral surface of the cylindrical inserting member 320. In this arrangement, when the water repellant filter is interposed between the inner peripheral surface of the air hole and the outer peripheral surface of the cylindrical inserting member 320, the water repellant filter is pressed by the inner peripheral surface of the air hole and forced into the through hole 320a, thereby being engaged therebetween. The through hole 320a shown in FIG. 10(a) may be formed, for example, by punching the side surface of the cylindrical inserting member 320, but it is not limited thereto. As shown in FIG. 10(b), the engagement can also be achieved by forming a notch 320b on the side surface of the cylindrical inserting member 320 and folding the notched portion inwardly of the cylindrical inserting member 320. The through hole 320a serves as an engaging portion.

When the cylindrical inserting member 320 has a flange 320c, as shown in FIG. 10(c), a notch 320d can be formed in this flange 320c. In other words, when placing the water repellant filter over the flange 320c, the water repellant filter engages with the notch 320d, thereby preventing displacement of the water repellant filter. When the notch 320d is formed on the flange 320c, the edge of the water repellant filter can be visually observed irrespective of the presence of the flange 320c.

As shown in FIG. 10(d), it is also preferable to form a notch 320e extending along the axis of the cylindrical inserting member 320. In this arrangement, when the water repellant filter is interposed between the inner peripheral surface of the air hole and the outer peripheral surface of the cylindrical inserting member 320, the water repellant filter engages the notch 320e, thereby preventing displacement of the water repellant filter.

As shown in FIG. 10(e), it is preferable to form a tapered portion 320f on the outer peripheral surface of the cylindrical inserting member 320 at the portion that comes into contact with the water repellant filter. In FIG. 10(e), the outer peripheral surface of the cylindrical inserting member 320 is a tapered portion 320f tapering in the direction away from the opened end 320g closed by the water repellant filter. However, it is not limited to this, and what is important is that the portion with which the water repellant filter comes into contact is tapered. In this arrangement, the water repellant filter is pulled in the direction away from the opened end 320g of the cylindrical inserting member 320 closed by the water repellant filter when it is interposed between the inner peripheral surface of the air hole and the outer peripheral surface of the cylindrical inserting member 320, thereby preventing displacement of the water repellant filter, and enhancing waterproofing at the opened end 320g of the cylindrical inserting member 320.

As shown in FIG. 10(f), it is also possible to roughen the outer surface of the cylindrical inserting member 320 by a knurling process. Another way of roughening is to use a sand blasting process. Either one of these processes can be employed. FIG. 10(f) shows a state in which the whole part of the outer surface of the cylindrical inserting member 320 is roughened, but it is not limited thereto but partial roughening is also possible.

Figure 11:
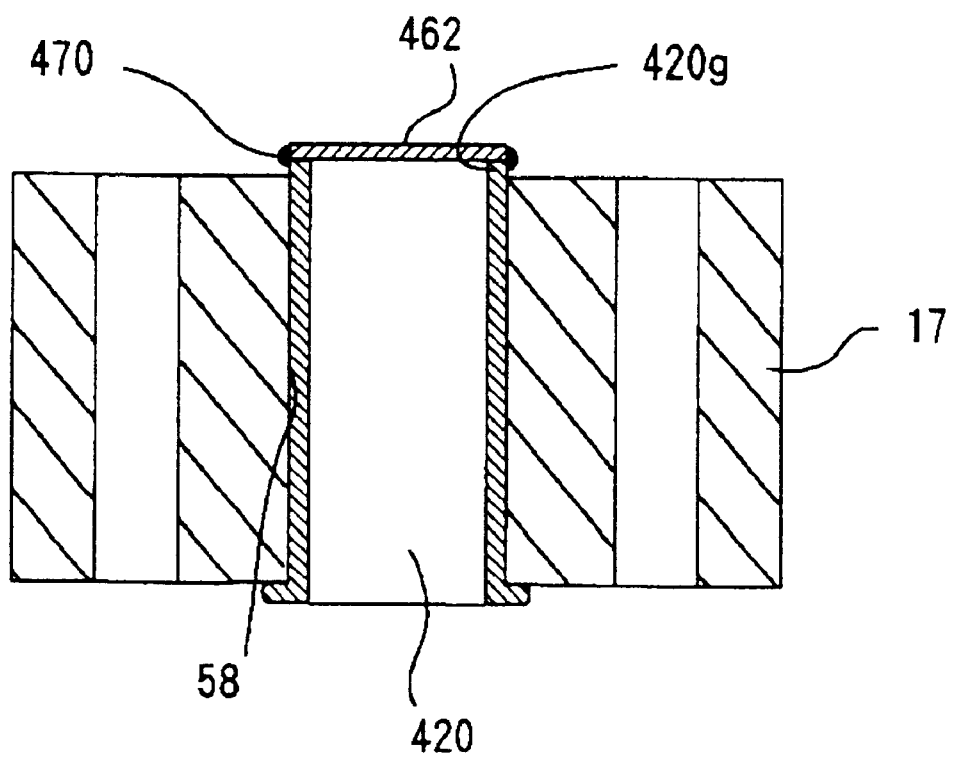
FIG. 11 is an explanatory drawing showing an alternative of the structure in the vicinity of the air hole.
Figure 12:
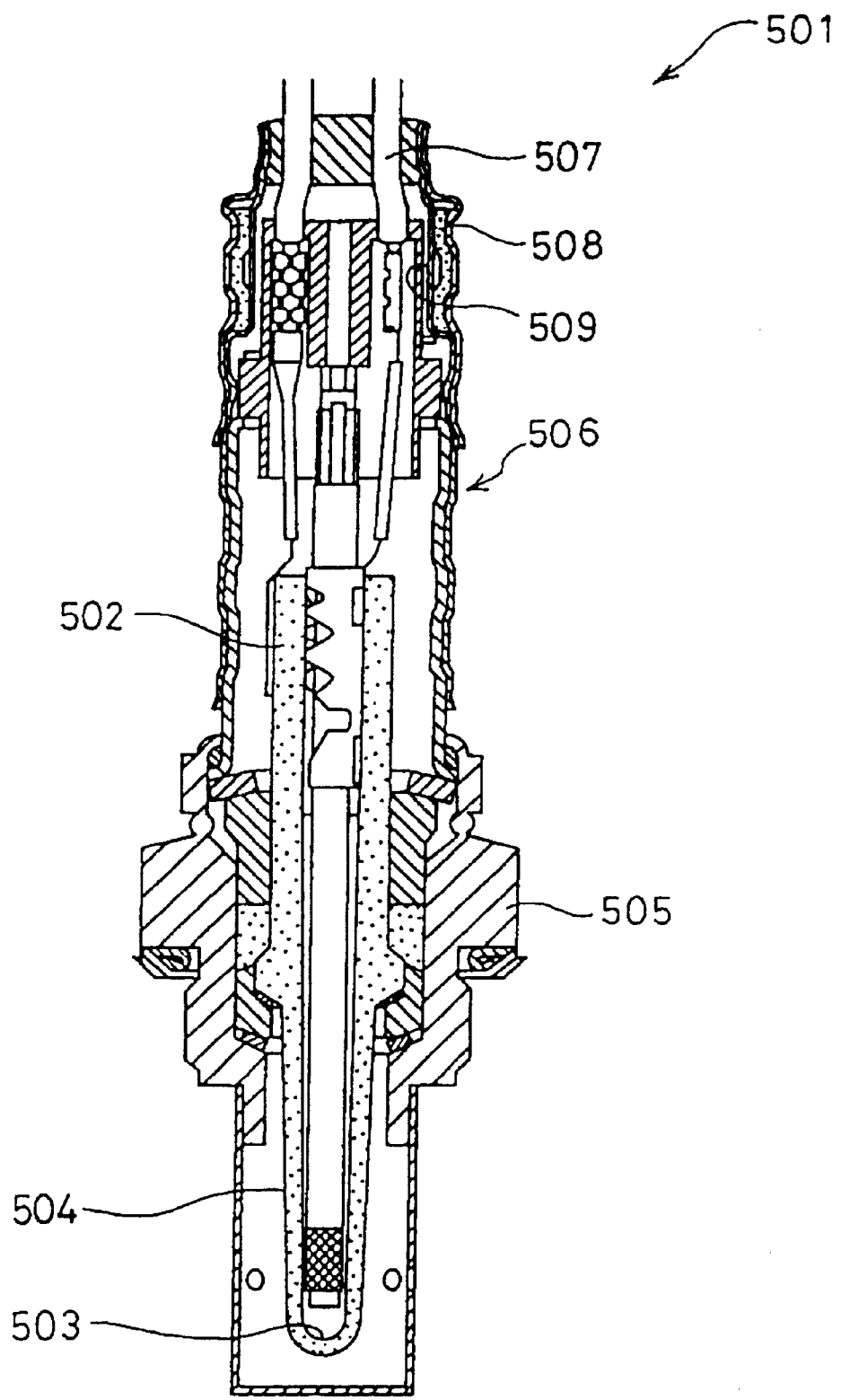
FIG. 12 is an explanatory drawing showing the oxygen sensor as an example of the related art.

In addition, as shown in FIG. 11, it is also possible to close the outer end 420g of the cylindrical inserting member 420 by adhering the circular water repellant filter 462 of almost the same diameter as the outer diameter of the opened end 420g integrally thereto using adequate adhesives or by welding 470, and press-fitting the cylindrical inserting member 420 into the insertion hole 58 of the sealing member 17.

In the embodiments or alternatives described above, it is preferable to apply a hydrophilic material such as resin to the upper surface of the sealing member 17 in advance, thereby preventing the filtering function of the water repellant filter from being deteriorated by being covered on its whole surface by water.

While the invention has been described in detail and with reference to specific embodiments thereof, it will be apparent to one skilled in the art that various changes and modifications can be made therein without departing from the spirit and scope thereof.

This application is based on Japanese Patent Application Nos. Hei. 11-346362 filed Dec. 6, 1999 and 2000-18576 filed Jan. 27, 2000, which are incorporated herein in their entirety.

What is claimed is:

1. A gas sensor comprising:
    a detecting element having electrodes on first and second surfaces of an oxygen ion conductive solid-state electrolyte;
    a main fitting having a fitting portion to be fitted into a mounting hole formed on a wall of a pipe defining a flow path for a gas-to-be-measured for holding said detecting element in such manner that said first surface is disposed via said mounting hole at an inner position of said pipe with respect to said fitting portion;
    a cylindrical cover of which one end is connected to an outer position of said pipe with respect to the fitting portion of said main fitting and the other end is provided with a cylindrical sealing member, said sealing member having an air hole extending therethrough in an axial direction for introducing air to said second surface and a through hole through which leads connected to the electrodes of said detecting element pass; and
    a gas permeable water repellant filter for closing said air hole, characterized in that said water repellant filter is formed in a sheet shape and mounted on said air hole by means of an inserting member inserted into said air hole and said water repellant filter is interposed between an outer peripheral surface of said inserting member and an inner peripheral surface of said air hole so as to close an open end of said inserting member.

2. The gas sensor as claimed in claim 1, characterized in that the inserting member is provided on its outer peripheral surface at the portion that contacts the water repellant filter with an engaging portion for engaging the water repellant filter when interposing the water repellant filter between the inserting member and the inner peripheral surface of the air hole.

3. The gas sensor as claimed in claim 2, characterized in that said water repellant filter is provided in said air hole in such manner that the edge portion thereof can be visually observed.

4. The gas sensor as claimed in claim 1, characterized in that said water repellant filter is provided in said air hole in such manner that the edge portion thereof can be visually observed.

5. The gas sensor as claimed in claim 1, further comprising an outer fitting member formed to be fitted on the outer periphery of said inserting member, with the water repellant filter interposed between the inner peripheral surface of said outer fitting member and the outer peripheral surface of said inserting member.

6. The gas sensor as claimed in claim 5, characterized in that said water repellant filter is interposed between the outer peripheral surface of the opened end of said inserting member closed by said water repellant filter and the inner peripheral surface of said outer fitting member.

7. The gas sensor as claimed in claim 6, characterized in that said inserting member is provided on its outer peripheral surface with a limiting portion for limiting the movement of said outer fitting member along the axis of said inserting member.

8. The gas sensor as claimed in claim 5, characterized in that said inserting member is provided on its outer peripheral surface with a limiting portion for limiting the movement of said outer fitting member along the axis of said inserting member.

9. The gas sensor as claimed in claim 5, characterized in that said outer fitting member and said inserting member are constructed so that they can be brought in direct contact with one another.

10. The gas sensor as claimed in claim 5, characterized in that said water repellant filter is fixed to said inserting member in such manner that the edge portion thereof can be visually observed.

11. The gas sensor as claimed in claim 1, characterized in that the portion of the outer surface of said inserting member being brought into contact with said water repellant filter is roughened.

12. The gas sensor as claimed in claim 1, characterized in that the portion of the outer surface of said inserting member being brought into contact with said water repellant filter is tapered in a direction away from the open end to be closed by said water repellant filter.

13. The gas sensor as claimed in claim 1, characterized in that the open end of said inserting member closed by said water repellant filter projects from the opened end of said air hole facing toward the outside portion of said gas sensor.

14. The gas sensor as claimed in claim 1, characterized in that said water repellant filter has anisotropic property in the extent of shrinkage by heat and is formed longer in a direction in which said filter is apt to shrink.

15. The gas sensor as claimed in claim 14, characterized in that said filter is formed in an oval shape having a long axis in said direction in which the filter is apt to shrink and a short axis in a direction orthogonal thereto.

16. The gas sensor as claimed in claim 1, characterized in that said air hole is formed coaxially with said sealing member and that said inserting member is formed of a material harder than that of said sealing member.

17. The gas sensor as claimed in claim 1, characterized in that said inserting member is provided on its outer periphery with a flange for engaging said sealing member.

18. The gas sensor as claimed in claim 17, characterized in that said flange engages with an engaging portion formed within said air hole.

19. The gas sensor as claimed in claim 17, characterized in that said flange is provided with a notch.

20. The gas sensor as claimed in claim 1, characterized in that said water repellant filter is oil repellant.

21. The gas sensor as claimed in claim 1, characterized in that a plurality of said water repellant filters are provided overlaying one another along the axis of said air hole.

22. The gas sensor as claimed in claim 1, characterized in that the outer surface of said sealing member facing toward the outside portion of said gas sensor has a convex shape.

23. The gas sensor as claimed in claim 22, characterized in that said outer surface projects furthest at the open end of said air hole facing the outside portion of said gas sensor.

24. The gas sensor as claimed in claim 1, characterized in that said water repellant filter is adhered on its outer periphery to said open end of said inserting member in such manner that said water repellant filter covers an open end of said inserting member, and said inserting member is a cylindrical inserting member.

25. A gas sensor comprising:

a detecting element having electrodes on first and second surfaces of an oxygen ion conductive solid-state electrolyte;

a main fitting having a fitting portion to be fitted into a mounting hole formed on a wall of a pipe defining a flow path for a gas-to-be-measured for holding said detecting element in such a manner that said first surface is disposed via said mounting hole exposed to the inside of said pipe;

a cover including a gas permeable sealing member having an air hole; and a gas permeable water repellant filter for closing said air hole;

wherein said water repellant filter is formed in a sheet-shape and mounted in said air hole via an inserting member inserted into said air hole, said water repellant filter is interposed between an outer peripheral surface of said inserting member and an inner peripheral surface of said air hole so as to close an open end of said inserting member; and one end of said cover being connected to the fitting portion of said main fitting remote from said pipe and the other end provided with said gas permeable sealing member having said air hole for introducing air to said second surface, said sealing member further comprising a through hole through which leads connected to the electrodes of said detecting element pass.

* * * * *